United States Patent
Van Krieken et al.

(10) Patent No.: US 12,398,047 B2
(45) Date of Patent: Aug. 26, 2025

(54) METHOD FOR PURIFYING MAGNESIUM CHLORIDE SOLUTIONS

(71) Applicant: PURAC BIOCHEM B.V., Gorinchem (NL)

(72) Inventors: Jan Van Krieken, Gorinchem (NL); Fesia Lestari Laksmana, Gorinchem (NL)

(73) Assignee: PURAC Biochem BV, Gorinchem (NL)

( * ) Notice: Subject to any disclaimer, the term of this patent is extended or adjusted under 35 U.S.C. 154(b) by 462 days.

(21) Appl. No.: 17/792,354

(22) PCT Filed: Jan. 15, 2021

(86) PCT No.: PCT/EP2021/050810
§ 371 (c)(1),
(2) Date: Jul. 12, 2022

(87) PCT Pub. No.: WO2021/144423
PCT Pub. Date: Jul. 22, 2021

(65) Prior Publication Data
US 2023/0059919 A1    Feb. 23, 2023

(30) Foreign Application Priority Data
Jan. 15, 2020   (EP) .................... 20151907

(51) Int. Cl.
| | |
|---|---|
| *C01F 5/10* | (2006.01) |
| *B01D 9/00* | (2006.01) |
| *C01F 5/30* | (2006.01) |
| *C07C 59/08* | (2006.01) |
| *C07D 319/12* | (2006.01) |
| *C12P 7/56* | (2006.01) |

(52) U.S. Cl.
CPC .............. *C01F 5/30* (2013.01); *B01D 9/0022* (2013.01); *B01D 9/0031* (2013.01); *C01F 5/10* (2013.01); *C07C 59/08* (2013.01); *C07D 319/12* (2013.01); *C12P 7/56* (2013.01); *B01D 2009/0086* (2013.01)

(58) Field of Classification Search
CPC ..................... C01F 5/10; C12P 7/56
See application file for complete search history.

(56) References Cited

U.S. PATENT DOCUMENTS

| | | |
|---|---|---|
| 2015/0044741 A1 | 2/2015 | Cerda Baro et al. |
| 2017/0218408 A1 | 8/2017 | Baets et al. |
| 2019/0194029 A1 | 6/2019 | De Vries et al. |

FOREIGN PATENT DOCUMENTS

| | | |
|---|---|---|
| EP | 0 261 572 A1 | 3/1988 |
| WO | 00/17378 A2 | 3/2000 |
| WO | 2013/093028 A1 | 6/2013 |
| WO | 2016/128501 A1 | 8/2016 |

OTHER PUBLICATIONS

Apr. 22, 2021 International Search Report issued in Patent Application No. PCT/EP2021/050810.
Apr. 22, 2021 Written Opinion of the International Searching Authority issued in Patent Application No. PCT/EP2021/050810.
Benthin, S. et al. "Production of optically pure D-lactate by lactobacillus bulgaricus and purification by crystallisation and liquid/liquid extraction.", Applied Microbiology and Biotechnology, Springer Berlin Heidelberg, (1995), vol. 42, No. 6, pp. 826-829.
Translation of Aug. 8, 2023 Office Action issued in Japanese Patent Application No. 2022-542493.
Jun. 11, 2024 Office Action issued in European Patent Application No. 21701080.0.

*Primary Examiner* — Tekchand Saidha
(74) *Attorney, Agent, or Firm* — Sunit Talapatra; Foley & Lardner LLP

(57) ABSTRACT

A process for removing lactic acid from an aqueous lactic acid-containing magnesium chloride solution, the weight ratio of magnesium chloride to lactic acid in the aqueous lactic acid-containing magnesium chloride solution being at least 1:1, the process including the steps of subjecting the aqueous lactic acid-containing magnesium chloride solution to an evaporation step, resulting in the formation of a slurry of MgCl2·MgL2·4H2O in an aqueous magnesium chloride solution, then subjecting the slurry to a solid-liquid separation step, to separate the solid MgCl2·MgL2·4H2O from the aqueous magnesium chloride solution, resulting in the removal of lactic acid from the aqueous lactic acid-containing magnesium chloride solution in the form of MgCl2·MgL2·4H2O. The process makes it possible to efficiently remove lactic acid from aqueous lactic acid-containing magnesium chloride solutions, resulting in magnesium chloride solutions with a low lactic acid content which can be further processed as desired.

9 Claims, 2 Drawing Sheets

METHOD FOR PURIFYING MAGNESIUM CHLORIDE SOLUTIONS

BACKGROUND

The present invention pertains to a process for purifying magnesium chloride solutions, in particular magnesium chloride solutions containing limited amounts of lactic acid. The invention also pertains to a method for manufacturing lactic acid through a fermentation process.

Lactic acid can be manufactured via fermentation of a carbon source, such as carbohydrates or glycerol, by microorganisms. In such a fermentation process a carbohydrate source is typically fermented by means of a micro-organism to form lactic acid. The liquid wherein the carbohydrate source is fermented is called the fermentation broth or the fermentation medium. The formation of lactic acid during fermentation will result in a decrease of the pH of the fermentation broth. Since such a decrease in pH can damage the micro-organism's metabolic process, it is common practice to add a neutralizing agent, i.e. a base, in the fermentation media in order to neutralize the pH. As a result, lactic acid produced in the fermentation media is typically present in the form of a lactate salt.

To recover the lactic acid from the fermentation medium after fermentation, downstream processing is required. One of the steps in downstream processing is an acidification step, wherein the lactate salt is contacted with an inorganic acid in an aqueous medium resulting in the formation of lactic acid and an inorganic salt. For example, if the lactate salt in the fermentation medium is a magnesium salt, an acidification with HCl will result in the formation of a solution containing dissolved lactic acid and dissolved magnesium chloride.

The next step is then to separate the lactic acid from the magnesium chloride solution. As both lactic acid and magnesium chloride have a high solubility in water, this separation is not straightforward.

WO00/17378 describes manufacture of lactic acid through fermentation, pH adjustment with Ca(OH)2 or Mg(OH)2, addition of HCl, and extraction of the lactic acid from the magnesium chloride solution with a solvent selected from amines, alcohols, and ethers, preferably isoamyl alcohol, diisopropyl ether, and Alamine 336. The solvent containing the lactic acid is then contacted with water to generate a lactic acid solution, which is processed further.

WO2013/093028 describes extraction of lactic acid from a magnesium chloride solution using an extractant selected from the group of C5+ ketones, diethylether, and methyl-tertiary-butyl ether, thereby obtaining an organic lactic acid solution and a waste magnesium chloride solution.

A problem that occurs in this extraction process is that the extraction of lactic acid from the magnesium chloride solution will not be complete. Limited amounts of lactic acid will remain in the magnesium chloride solution. This is disadvantageous for two reasons. In the first place, the presence of lactic acid in the magnesium chloride solution will reduce the yield of lactic acid for the overall process. In the second place, the lactic acid present in the magnesium chloride solution has been found to interfere with further processing of the magnesium chloride solution, which requires the solution to be highly concentrated. Removal of the lactic acid has been found difficult, on the one hand because the amount of lactic acid in the magnesium chloride solution will be relatively small as compared to the amount of magnesium chloride in the solution and on the other hand by the fact that both magnesium chloride and lactic acid have a high solubility in water.

Accordingly, there is need in the art for a process for removing limited amounts of lactic acid from a magnesium chloride solution. The present invention provides such a process.

SUMMARY

The present invention pertains to a process for removing lactic acid from an aqueous lactic acid-containing magnesium chloride solution, the weight ratio of magnesium chloride to lactic acid in the aqueous lactic acid-containing magnesium chloride solution being at least 1:1, the process comprising the steps of
  subjecting the aqueous lactic acid-containing magnesium chloride solution to an evaporation step, resulting in the formation of a slurry of $MgCl_2 \cdot MgL_2 \cdot 4H_2O$ in an aqueous magnesium chloride solution,
  subjecting the slurry to a solid-liquid separation step, to separate the solid $MgCl_2 \cdot MgL_2 \cdot 4H_2O$ from the aqueous magnesium chloride solution. The separation of the solid $MgCl_2 \cdot MgL_2 \cdot 4H_2O$ from the aqueous magnesium chloride solution results in the removal of lactic acid from the aqueous lactic acid-containing magnesium chloride solution in the form of $MgCl_2 \cdot MgL_2 \cdot 4H_2O$.

It has been found that the process of the present invention makes it possible to efficiently remove lactic acid from aqueous lactic acid-containing magnesium chloride solutions, resulting in magnesium chloride solutions with a low lactic acid content which can be further processed as desired. The solid $MgCl_2 \cdot MgL_2 \cdot 4H_2O$ can also be processed as desired, e.g., by providing it to an acidification step where magnesium lactate is reacted with HCl. Further advantages from the present invention and specific embodiments thereof will become apparent from the further specification.

DETAILED DESCRIPTION

Figure 1:
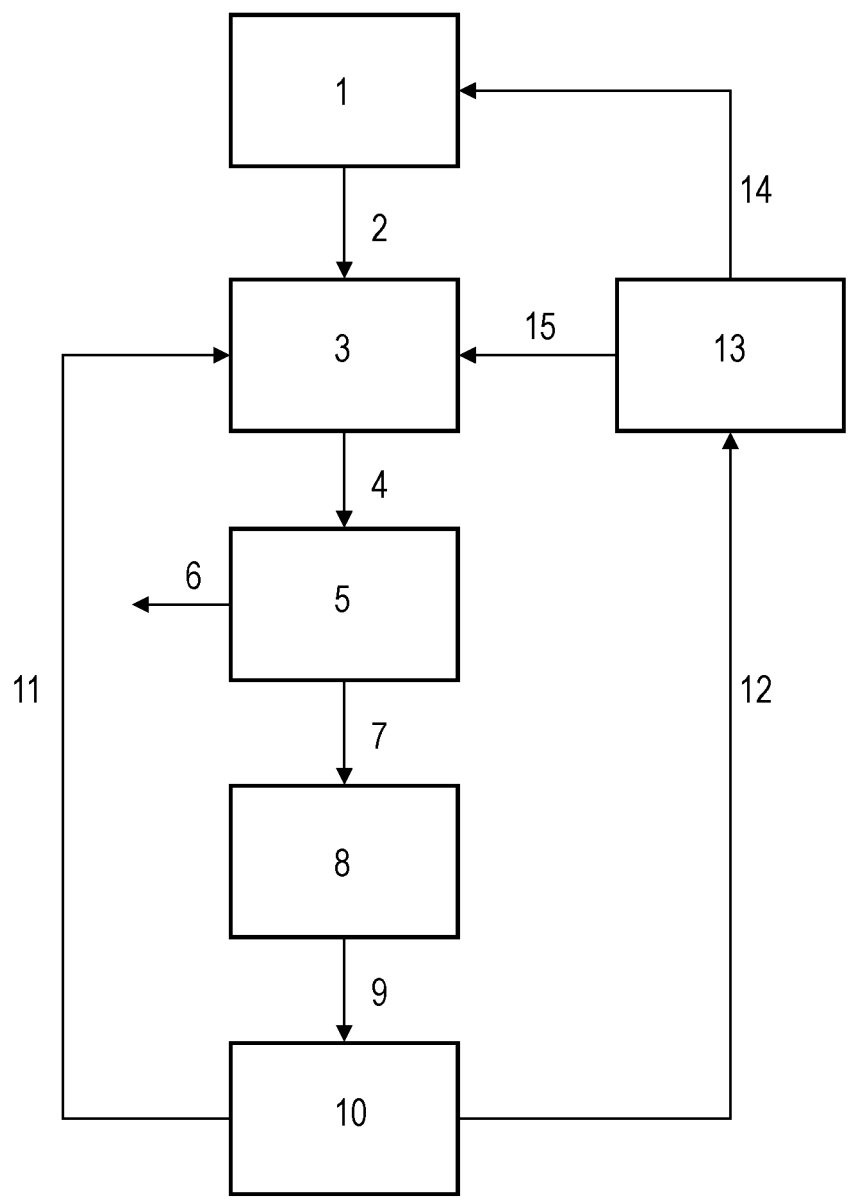
FIG. 1 illustrates an embodiment of the method for manufacturing lactic acid according to the invention.

The present invention will be discussed in more detail below.

The crux of the present invention resides in the recognition that to separate lactic acid and magnesium chloride both having a high solubility in water, a double salt $MgCl_2 \cdot MgL_2 \cdot 4H_2O$ can be created which has a low solubility in water and which actually can be used as a vehicle to remove lactic acid from magnesium chloride solutions.

Accordingly, the present invention can be worded as a process for removing lactic acid from an aqueous lactic acid-containing magnesium chloride solution, the process comprising the steps of
  subjecting the aqueous lactic acid-containing magnesium chloride solution to an evaporation step, resulting in the formation of a slurry, and
  subjecting the slurry to a solid-liquid separation step, wherein the process is characterized in that
  the weight ratio of magnesium chloride to lactic acid in the aqueous lactic acid-containing magnesium chloride solution is at least 1:1, the evaporation step is resulting in the formation of a slurry of $MgCl_2 \cdot MgL_2 \cdot 4H_2O$ in an aqueous magnesium chloride solution, and the solid-liquid separation step is to separate the solid $MgCl_2 \cdot MgL_2 \cdot 4H_2O$ from the aqueous magnesium chloride solution, resulting in the removal of lactic acid from the aqueous lactic acid-containing magnesium chloride solution in the form of $MgCl_2 \cdot MgL_2 \cdot 4H_2O$.

The aqueous lactic-acid containing magnesium chloride solution to be processed in accordance with the present invention has a weight ratio of magnesium chloride to lactic acid of at least 1:1. If the weight ratio of magnesium chloride to lactic acid is below this value, the efficiency of the process will decrease. As higher ratios lead to increased process efficiency, in particular as regards the solids content of the product, it is preferred to operate at higher magnesium chloride to lactic acid weight ratios, such as at least 1.5:1. Alternatively it may be preferred that the weight ratio of magnesium chloride to lactic acid is at least 2:1. More specifically, it may be preferred for the weight ratio of magnesium chloride to lactic acid to be at least 4:1, in particular at least 5:1, more in particular at least 6:1. If a magnesium chloride solution is to be processed wherein the magnesium chloride to lactic acid is below the desired operating value, the solution may first be subjected to a lactic acid removal step, for example by means of extraction, membrane separation, ion exchange, ion absorption, or adsorption, to increase the magnesium chloride to lactic acid weight ratio to the desired operating value.

If the amount of lactic acid in the lactic acid-containing magnesium chloride medium is too low, removing lactic acid through the process according to the invention may not be economically attractive. Accordingly, the weight ratio of magnesium chloride to lactic acid will generally be at most 70:1, in particular at most 50:1, more in particular at most 40:1, in some embodiments at most 20:1.

The absolute concentrations of the magnesium chloride and lactic acid in the lactic-acid containing magnesium chloride solution to be processed in accordance with the present invention are less relevant, as the first step in the process is the removal of water, resulting in an increase of the concentration. In general, the magnesium chloride concentration of the solution will be in the range of 5 to 35 wt. %, in particular in the range of 10-35 wt. %, more in particular in the range of 15-35 wt. %. The amount of lactic acid can be determined from the ratios specified above.

The lactic-acid containing magnesium chloride solution is an aqueous solution. It may contain limited amounts of further compounds derived, e.g., from previous steps in the manufacture of the solution, but this is not necessary and not desired.

For example, in one embodiment, as will be discussed in more detail below, the aqueous lactic-acid containing magnesium chloride solution used as starting material in the present invention can be obtained by processing of a fermentation broth comprising magnesium lactate. A fermentation broth comprising magnesium lactate may be acidified with hydrogen chloric acid, and subjected to separation to form lactic acid and a solution containing predominantly magnesium chloride and limited amount of lactic acid. This latter solution may be used as starting material in the process according to the invention. In this case, it is preferred for the solution to contain no, or quite limited amounts of contaminants resulting from the fermentation process the acidification step, or the separation step, as these impurities may also interfere in an undesired manner with the further processing of the magnesium chloride solution by the process according to the invention. Accordingly, it is preferred for the aqueous lactic-acid containing magnesium chloride solution to contain less than 10 wt. % of other components (than water, magnesium chloride, lactic acid, and salts thereof), preferably less than 5 wt. % and more preferably less than 1 wt. %. The presence of volatile organic compounds (that is, compounds which will evaporate from the solution under evaporation conditions), e.g., extractants from a previous separation step by means of an extraction process may be less detrimental than other components, as they will be removed in the evaporation step. Accordingly, in one embodiment, the lactic-acid containing magnesium chloride solution contains less than 8 wt. % of volatile organic compounds and less than 4 wt. % of other compounds (not being lactic acid, magnesium chloride, double salts thereof, or volatile organic compounds). It is preferred for the amount of volatile organic compounds to be at most 6 wt. %, in particular at most 4 wt. %, more in particular at most 2 wt. %. It is preferred for the amount of other compounds to be at most 3 wt. %, in particular at most 2 wt. %, more in particular at most 1 wt. %.

The aqueous lactic-acid containing magnesium chloride solution is subjected to an evaporation step, resulting in the formation of a slurry of $MgCl_2 \cdot MgL_2 \cdot 4H_2O$ in a magnesium chloride solution. In the evaporation step, water is removed resulting in the increase of the concentrations of lactic acid and magnesium chloride to a value above the solubility product of $MgCl_2 \cdot MgL_2 \cdot 4H_2O$.

Therefore, the evaporation step will result in the formulation of a slurry of $MgCl_2 \cdot MgL_2 \cdot 4H_2O$ in a magnesium chloride solution. The concentration of magnesium chloride at which precipitation of $MgCl_2 \cdot MgL_2 \cdot 4H_2O$ will start will depend on the prevailing conditions, with higher lactic acid concentrations and magnesium chloride concentration promoting precipitation. In general, the formation of solid $MgCl_2 \cdot MgL_2 \cdot 4H_2O$ will start even when the concentration of lactic acid is less than 1 wt. %, when the magnesium chloride concentration is above 31 wt. %, in particular above 35 wt. %.

It is generally preferred for the temperature during the evaporation step to be in the range of 50-200° C., in particular in the range of 80-150° C. A higher temperature is preferred to increase solubility of $MgCl_2$, and therewith the concentration of $MgCl_2$ in the product solution. Surprisingly, it has been found that the selection of the higher temperatures indicated above has only a limited effect on the solubility of $MgCl_2 \cdot MgL_2 \cdot 4H_2O$. A higher temperature will thus lead to the formation of more solid $MgCl_2 \cdot MgL_2 \cdot 4H_2O$, as the higher magnesium chloride concentration will force more $MgCl_2 \cdot MgL_2 \cdot 4H_2O$ from the solution. Further, a higher temperature aids in the removal of water.

The evaporation step can be carried out at atmospheric pressure, or even at increased pressure. However, it is preferred for the evaporation step to be carried out at reduced pressure, as this will allow efficient evaporation at acceptable temperatures. Therefore, in one embodiment, the evaporation of water is carried out at a pressure of 0.01-0.9 bar, in particular in the range of 0.01-0.35 bar.

The evaporation is continued until the desired amount of $MgCl_2 \cdot MgL_2 \cdot 4H_2O$ has been precipitated. A first factor influencing this is the concentration of dissolved magnesium chloride in the liquid. In general, the evaporation will be continued until the solution has a magnesium chloride concentration in the range of 30-47 wt. %, in particular 33-45 wt. %, more in particular in the range of 38-45 wt. %. If evaporation is stopped at a lower concentration, the precipitation of $MgCl_2 \cdot MgL_2 \cdot 4H_2O$ will be insufficient. It the evaporation is continued to a magnesium chloride concentration which is too high, there is a risk of precipitation of magnesium chloride, which is not desired in the present process.

The evaporation step can be carried out in a single step or in multiple steps. Where the concentration of the starting solution is relatively low and/or the weight ratio between $MgCL_2$ and lactic acid is relatively high, e.g., at least 6:1, more in particular at least 8:1, it may be attractive to carry out the evaporation in multiple steps.

The product obtained after the evaporation step is a slurry of $MgCl_2 \cdot MgL_2 \cdot 4H_2O$ in a magnesium chloride solution. Depending on the amount of lactic acid in the starting solution, and the concentration of $MgCl_2$ in the product solution, the slurry can contain at least 2 wt. % $MgCl_2 \cdot MgL_2 \cdot 4H_2O$, in particular at least 4 wt. %. In general, the slurry will contain at most 50 wt. % of $MgCl_2 \cdot MgL_2 \cdot 4H_2O$, in particular at most 40 wt. % of $MgCl_2 \cdot MgL_2 \cdot 4H_2O$, in particular at most 30 wt. % of $MgCl_2 \cdot MgL_2 \cdot 4H_2O$, in particular at most 25 wt. % of $MgCl_2 \cdot MgL_2 \cdot 4H_2O$, in some embodiments at most 20 wt. % of $MgCl_2 \cdot MgL_2 \cdot 4H_2O$.

The slurry is subjected to a solid-liquid separation in which the $MgCl_2 \cdot MgL_2 \cdot 4H_2O$ is separated from the magnesium chloride solution. During the solid-liquid separation, the slurry preferably has a temperature similar to that of the evaporation step. It is hereby understood that a similar temperature implies that the temperature difference between the slurry during the evaporation step and the solid-liquid separation is less than 20° C. etc. The solid-liquid separation can be carried out by methods known in the art, e.g., via filtration or centrifugation, or through a combination thereof.

The magnesium chloride solution obtained from the separation step generally has a magnesium chloride concentration in the range of 35-47 wt. %. At concentrations below 35 wt. % the precipitation of lactic acid as $MgCl_2 \cdot MgL_2 \cdot 4H_2O$ may not have taken place to the desired extent, leaving a too large amount of lactic acid in the solution. At concentrations above 47 wt. % magnesium chloride may have precipitated from the solution. It may be preferred for the magnesium chloride concentration to be at least 37 wt. %, in particular at least 39 wt. %, and/or at most 47 wt. %, in particular at most 45 wt. %.

The lactic acid concentration in the magnesium chloride solution obtained from the separation step will generally be at most 1 wt. %, in particular at most 0.5 wt. %, more in particular at most 0.2 wt. %.

In one embodiment, the invention pertains to a process wherein a lactic acid-containing magnesium chloride solution with a lactic acid concentration of 0.5-7 wt. % and a magnesium chloride concentration of 15-25 wt. % is subjected to one or more evaporation steps, resulting in a slurry of 4-40 wt. % $MgCl_2 \cdot MgL_2 \cdot 4H_2O$ in a magnesium chloride solution with a magnesium chloride concentration of 35-47 wt. %, and the slurry is subjected to a solid-liquid separation step resulting in solid $MgCl_2 \cdot MgL_2 \cdot 4H_2O$ and a magnesium chloride solution with a lactic acid concentration of less than 0.5 wt. % and preferably less than 0.2 wt. %.

This process has been found to have commercial utility.

The process according to the invention is particularly attractive for incorporation into a method for manufacturing lactic acid using a fermentation step. Hence, in this embodiment, the process for removing lactic acid from an aqueous lactic acid-containing magnesium chloride solution is used to separate lactic acid from an aqueous lactic acid-containing magnesium chloride solution that is obtained by a fermentation process. Preferably the aqueous lactic acid-containing magnesium chloride solution is the effluent obtained by

- subjecting a carbon source to a fermentation step to form lactic acid, which fermentation step comprises the steps of fermenting a carbon source by means of a microorganism in a fermentation medium to form lactic acid,
- neutralising at least part of the lactic acid by adding a magnesium base selected from magnesium oxide and magnesium hydroxide to the fermentation medium, thereby obtaining magnesium lactate,
- subjecting the magnesium lactate to an acidification step wherein the magnesium lactate is contacted with HCl in an aqueous environment to form an aqueous mixture comprising lactic acid and magnesium chloride,
- subjecting the aqueous mixture comprising lactic acid and magnesium chloride to a separation step, to form an effluent comprising lactic acid and an aqueous lactic-acid containing magnesium chloride solution, and recovering the effluent comprising lactic acid from the process.

Hence, in one embodiment, the invention thus pertains to a process for the manufacture of lactic acid comprising the steps of

- subjecting a carbon source to a fermentation step to form lactic acid, which fermentation step comprises the steps of fermenting a carbon source by means of a microorganism in a fermentation medium to form lactic acid
- neutralising at least part of the lactic acid by adding a magnesium base selected from magnesium oxide and magnesium hydroxide to the fermentation medium, thereby obtaining magnesium lactate,
- subjecting the magnesium lactate to an acidification step wherein the magnesium lactate is contacted with HCl in an aqueous environment to form an aqueous mixture comprising lactic acid and magnesium chloride,
- subjecting the aqueous mixture comprising lactic acid and magnesium chloride to a separation step, to form an effluent comprising lactic acid and an aqueous lactic-acid containing magnesium chloride solution, and recovering the effluent comprising lactic acid from the process,
- subjecting the lactic acid-containing magnesium chloride solution, the weight ratio of magnesium chloride to lactic acid in the aqueous lactic acid-containing magnesium chloride solution being at least 1:1, to an evaporation step, resulting in the formation of a slurry of $MgCl_2 \cdot MgL_2 \cdot 4H_2O$ in a magnesium chloride solution,
- subjecting the slurry of $MgCl_2 \cdot MgL_2 \cdot 4H_2O$ in a magnesium chloride solution to a solid-liquid separation step, to isolate the solid $MgCl_2 \cdot MgL_2 \cdot 4H_2O$ from the aqueous solution magnesium chloride solution.

The solid $MgCl_2 \cdot MgL_2 \cdot 4H_2O$ can be recycled at least in part to the acidification step. In the acidification step, the $MgCl_2 \cdot MgL_2 \cdot 4H_2O$ will dissolve in reaction with HCl to form dissolved lactic acid and magnesium chloride.

The magnesium chloride solution resulting from the solid-liquid separation of the slurry has a high magnesium chloride content and a low lactic acid content. It is therewith suitable for processing through thermal decomposition. In thermal decomposition the magnesium chloride is reacted with water (present in the aqueous solution) at high temperature to form solid MgO and gaseous HCl. If so desired the solid MgO can be recycled at least in part to the fermentation step, as such or after having been converted into magnesium hydroxide. The gaseous HCl can, if so desired, be recycled at least in part to the acidification step. The gaseous HCl can be recycled as such, or after having been dissolved in water to form an aqueous HCl solution.

The various steps in the integrated process which are additional to purification of the lactic acid-containing magnesium chloride solution will be discussed below.

In the first step a carbon source is subjected to a fermentation step to form lactic acid, which fermentation step comprises the steps of fermenting a carbon source by means of a micro-organism in a fermentation broth to form lactic acid and neutralizing at least part of the lactic acid by adding a magnesium base selected from magnesium oxide and magnesium hydroxide, thereby obtaining a magnesium lactate.

Fermentation processes for the manufacture of lactic acid are known in the art and require no further elucidation here. It is within the scope of the skilled person to select, using his common general knowledge, a suitable fermentation process, depending on the desired acid to be produced, the carbon source and the microorganism available.

The product of the fermentation process is a fermentation broth, which is an aqueous liquid comprising magnesium lactate, biomass, and optionally further components such as impurities like are sugars, proteins, and salts.

If so desired, the fermentation broth may be subjected to a biomass removal step, e.g., a filtration step, before further processing. This is generally preferred for improving product quality.

The magnesium lactate may be present as solution or in the solid form. The solid magnesium lactate may for example also be present in the form of a suspension or slurry. Another intermediate step may be separation of solid magnesium lactate from the fermentation broth, before, after, or simultaneous with biomass removal. The magnesium lactate may be present in the form of a wet cake that may be obtained for example after such a biomass removal step. Optionally, the magnesium lactate can be subjected to a washing step.

Another intermediate step may be subjecting the fermentation broth to a concentration step to increase the concentration of magnesium lactate in the composition before acidification. This step may be carried out before, after, or simultaneous with biomass removal.

Other intermediate steps, e.g., purification steps, may be carried out as desired, as will be evident to the skilled person. An example of a suitable process is a process wherein a fermentation broth comprising magnesium lactate and biomass is subjected to a biomass removal step, a step to remove solid magnesium lactate, a concentration step on the remaining liquid medium to form further solid magnesium lactate, and removal of the further solid magnesium lactate from the liquid medium. The two fractions of solid magnesium lactate can then be subjected to an acidification step, as will be discussed below.

The next step in the integrated process according to the invention is subjecting the magnesium lactate to an acidification step wherein the magnesium lactate is contacted with HCl in an aqueous environment to form an aqueous mixture comprising lactic acid and magnesium chloride.

There are various ways in which this step can be effected. The acidification step is typically conducted by bringing the lactate salt in contact with an acidic HCl solution. However, in some embodiments it may also be possible to contact the lactate salt with gaseous HCl.

The lactate salt may be in solid and/or dissolved form. In one embodiment, the lactate salt is provided in solid form. This solid magnesium lactate may also be present in the form of a suspension or slurry. Or it may be present in the form of a wet cake obtained after for example a filtration or centrifugation step with optional re-dilution or re-slurrying of the cake. In this case, the acidification step is conducted by bringing the lactate salt in contact with an acidic solution. The advantage of preparing the aqueous mixture from lactate salt in solid form is that very high lactic acid concentration can thus be obtained, such as a concentration of at least 15 wt. %, in particular at least 25 wt. %, up to, e.g. 50 wt. %, or up to e.g., 40 wt. %.

The lactate salt may also be in dissolved form, typically as part of an aqueous solution. In this case, the acidification step can be conducted by bringing the lactate salt in contact with an acidic solution or an acidic gas.

The acidification step may also be conducted on a mixture of lactic acid and lactate salt. Such a mixture may for example be obtained in a low pH fermentation. The mixture may for example be an aqueous suspension.

When acidification of the lactate salt is conducted by contacting it with an acidic HCl solution, it preferably has a HCl concentration as high as possible. Such a high HCl concentration will result in an aqueous mixture with a high lactic acid concentration, which is desirable. The HCl solution therefore comprises at least 5 wt. %, more preferably at least 10 wt. % and even more preferably at least 20 wt. % HCl, based on the total weight of the HCl solution.

Acidification is typically conducted using an excess of HCl. The excess is preferably small, such that the aqueous mixture obtained is not highly acidic, which may not be desirable in view of further processing such a mixture. For example, the excess of acid used may be such that the resulting aqueous mixture has a pH 2 or lower, preferably a pH of 0-1.

In case gaseous HCl is used, it may be contacted by bringing it in contact with a lactate solution or suspension. In particular, HCl gas may be blown through the solution or suspension.

Preferably, acidification is conducted at a temperature of 75° C. or less. At higher temperatures, it becomes uneconomical to adapt equipment to the harsh conditions of an acidic environment at high temperatures.

The acidification step results in the formation of an aqueous liquid comprising lactic acid and magnesium chloride. This aqueous liquid is subjected to a separation step, optionally after intermediate processing steps have been carried out such as a concentration step. Since the lactic acid will be dissolved in the aqueous liquid, separation can take place using any suitable separation technique, including extraction with a suitable extractant, membrane separation, ion exchange, ion absorption, or adsorption.

In case of extraction, it is important that the extractant, which may also be indicated as extraction agent, is substantially not miscible with water. The use of an extractant results in the formation of a two-phase system during the separation step which comprises a liquid organic layer comprising extraction agent and lactic acid and an aqueous layer which is a magnesium chloride solution containing minor amounts of lactic acid as contaminant.

Examples of suitable extractants are aliphatic and aromatic hydrocarbons, such as alkanes and aromatic compounds, ketones, and ethers. Mixtures of various compounds may also be used.

Examples of suitable aliphatic alkanes are C5-C10 straight chain, branched, or cyclic alkanes, e.g., octane, hexane, cyclohexane, 2-ethyl-hexane, and heptane. Examples of suitable aromatic compounds are C6-C10 aromatic compounds, e.g., toluene, xylenes, and ethylbenzene.

Examples of suitable ketones are C5+ ketones, more in particular C5-C8 ketones in the present invention. C5+ stands for ketones with at least 5 carbon atoms. The use of C9+ ketones is less preferred, The use of methyl-isobutyl-ketone (MIBK) has been found to be particularly attractive. Examples of suitable ethers are C3-C6 ethers, e.g., methyl tert-butyl ether (MTBE) and diethyl ether (DEE).

The organic layer and the aqueous layer can be separated using conventional liquid-liquid separation methods, e.g., decantation, settling, centrifugation, use of plate separators, use of coalescers, and use of hydrocyclones. Combination of different methods and apparatus may also be used.

The organic layer is a solution of lactic acid in the organic extractant. The lactic acid can be separated from the extractant as desired. In one embodiment this can be done by removing the extractant by evaporation. In another embodiment the carboxylic acid can be recovered from the extractant by an extraction with water or another aqueous liquid.

The lactic acid can be processed as desired. Examples of further processing steps are purification steps such as one or more of washing, active carbon treatment, recrystallization, distillation, and filtration. Where the carboxylic acid is lactic acid, it can be converted to lactide and polylactic acid (PLA). Methods for carrying out the various steps are known to the skilled person. The invention also pertains to lactic acid, lactide and polylactic acid obtainable, or obtained, by the methods described herein.

The lactic acid-containing magnesium chloride solution is subjected to the lactic acid removal step of the present invention as described above.

The magnesium chloride solution from which lactic acid has been removed can be subjected to the thermal decomposition step in a thermohydrolysis reactor, where the magnesium chloride reacts with water to form magnesium oxide and HCl. Suitable apparatuses for conducting the thermohydrolysis step, also indicated herein as thermal decomposition step, are known in the art. For example, a spray roaster or a fluid bed roaster can be used. Such apparatuses can for example be obtained at SMS Siemag, Andritz, Tenova, and/or JohnCockerill. The use of a spray roaster is preferred. A spray roaster has low energy costs (also compared to a fluid bed roaster), because it requires relatively low temperatures (as described below). A spray roaster was further found to produce reactive MgO particles, which are very suitable for use as a neutralizing agent in fermentation. Thermal decomposition is conducted at a temperature of a least 300° C., which is the minimum temperature at which MgCl2 decomposes. Preferably, thermal decomposition is conducted at a temperature of at least 350° C. Due to energy costs, the temperature is preferably below 1000° C., more preferably below 800° C., still more preferably below 600° C. In addition, using a too high temperature for the thermal decomposition step is undesirable, because it will reduce the reactivity of the MgO formed, such that it is less suitable for use as a neutralizing agent in fermentation. For example, the temperature at which thermal decomposition is conducted may be 350-600° C. or 400-500° C. The temperature mentioned is the temperature of the gases as they are removed from the unit.

Thermal decomposition as applied in the present invention is preferably conducted at a pressure of 0.1-10 bar. However, the use of elevated pressure may be undesirable, because of an increased risk of corrosion in the downstream units due to the HCl not being able to condense. Preferably, thermal decomposition is conducted at atmospheric pressure, in particular when using a roaster, to avoid unnecessary energy costs and the need for expensive high pressure equipment. A pressure in the range of 0.9-1 bar may be preferred to prevent venting of HCl.

As will be clear to the skilled person, preferences for various aspects of the present invention can be combined, unless they are mutually exclusive.

FIG. 1 illustrates an embodiment of the method for manufacturing lactic acid according to the invention. In FIG. 1, a fermentation step is carried out in fermentation reactor (1), which is provided with a carbon source and optionally further components such as nutrients through lines not shown. In the fermentation step a carbon source is fermented by means of a micro-organism in a fermentation broth to form lactic acid carboxylic acid and neutralizing at least part of the lactic acid by adding a magnesium base, thereby obtaining a magnesium lactate. The magnesium base is added through line (14). The fermentation broth comprising a magnesium lactate salt is provided to an acidification step (3) through line (2). Intermediate steps such as biomass removal, separation of the solid product, or concentration may be carried out, but are not shown. In the acidification step (3) the magnesium lactate is contacted with HCl in an aqueous environment to form an aqueous mixture comprising lactic acid and magnesium chloride.

The aqueous mixture comprising carboxylic acid and magnesium chloride is provided to a separation step (5) through line (4). The separation step may be carried out through extraction as described above. Separation step (5) results in an effluent comprising lactic acid and in a lactic-acid containing magnesium chloride solution. The product lactic acid is withdrawn through line (6), generally in the form of a lactic acid solution in the extractant. The lactic acid can be recovered from the extractant as described above, and further processed as described above (not shown). The lactic acid-containing magnesium chloride solution is withdrawn through line (7) and provided to evaporation step (8). In evaporation step 8, water is evaporated resulting in the formation of a slurry of $MgCl_2 \cdot MgL_2 \cdot 4H_2O$ in a magnesium chloride solution. The slurry is provided through line (9) to a separation step (10), where solid $MgCl_2 \cdot MgL_2 \cdot 4H_2O$ is separated from the magnesium chloride solution. The solid $MgCl_2 \cdot MgL_2 \cdot 4H_2O$ is withdrawn though line (11) and recycled to acidification step (3). The magnesium chloride solution is withdrawn through line (12) and provided to a thermal decomposition step (13). In the thermal decomposition step, the magnesium chloride solution is converted to solid MgO, which can be provided to the fermentation step through line (14), as such or after having been converted to $Mg(OH)_2$ after having been reacted with water.

The thermal decomposition step also generates HCl, which can be provided to the acidification step through line (15), in gaseous form, or after having been absorbed in an aqueous liquid in an absorption step (not shown).

As will be clear to the skilled person, preferences for various aspects of the present invention can be combined, unless they are mutually exclusive. In particular, the preferences described for the process for removing lactic acid from a lactic acid containing magnesium chloride solution also apply to the corresponding step in the process of manufacturing lactic acid.

The present invention is further illustrated by the following example, without being limited thereto or thereby.

EXAMPLES

Example 1

A ternary solid-liquid phase diagram of the system magnesium chloride—lactic acid—water was obtained at 20° C., 50° C. and 80° C. This diagram was constructed by measuring the solubility of mixtures of magnesium chloride hexahydrate ($MgCl_2 \cdot 6H_2O$), double crystallized (S)-Lactic acid crystals and demineralized water. The solubility lines were determined by adding the appropriate amounts of said chemicals to a glass vessel, heating the system to the appropriate temperature and stirring for about 30 minutes. Next a small amount of water or lactic acid solution was added to change the overall composition and the new system was stirred at least 10 minutes.

When it was observed that the solids did not dissolve, another small amount of water was added followed by stirring for at least 10 minutes. This was repeated until all solids had dissolved. Care was taken to allow for additional dissolution time close to the dissolution point.

Figure 2:
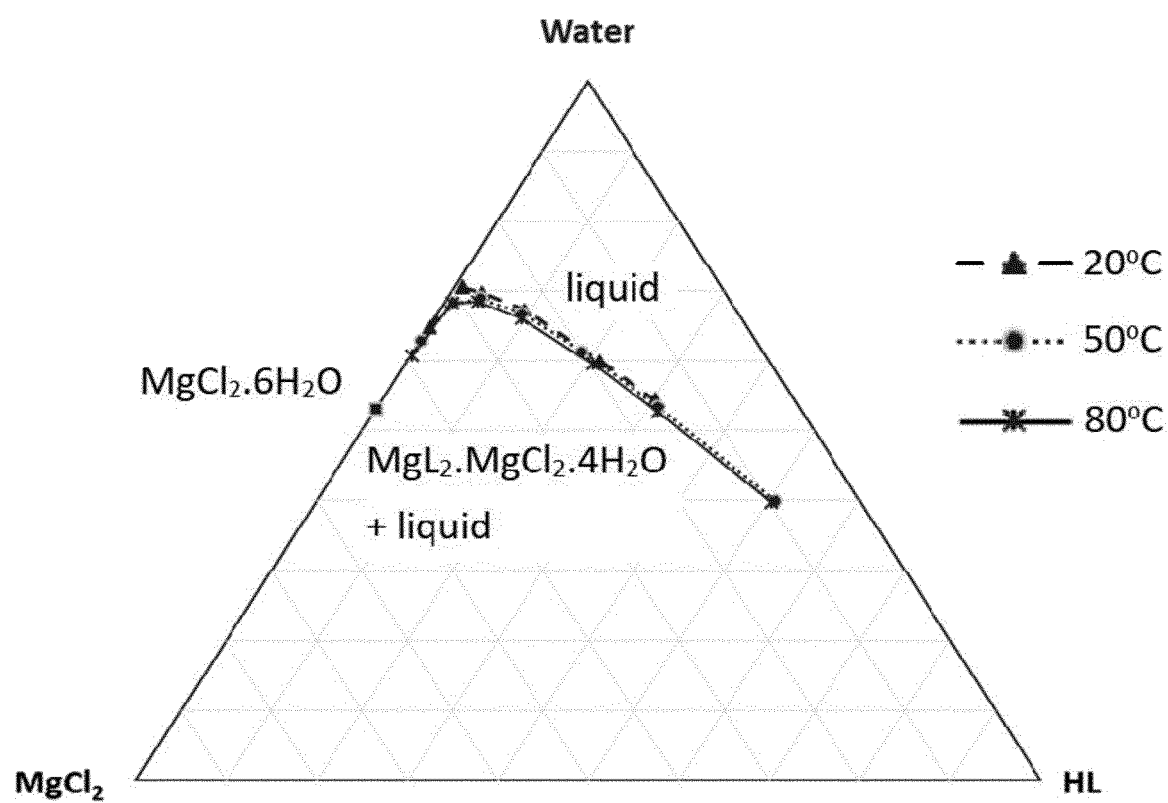
FIG. 2 is the ternary solid-liquid phase diagram of the system magnesium chloride-lactic acid-water at 20° C., 50° C. and 80° C. as described in Example 1.

After establishing the dissolution point, the composition was back-calculated from the initial masses and added water/chemicals. The result is the ternary solid-liquid phase diagram of the system magnesium chloride—lactic acid—water as depicted in FIG. 2.

The crystals formed during the above experiment were examined and magnesium chloride hydrate crystals were only observed in lactic acid free samples. The solubility of magnesium chloride crystals decreased significantly when lactic acid was added and needle shaped crystals were formed.

The needle shaped crystals were isolated by filtration (twice with separate samples), the filter cake was washed with ethanol to remove residual liquid material and dried at room temperature. The solids obtained were analysed to determine their composition. The lactate/lactic acid content was determined by HPLC. The organic acids were quantified by HPLC with a column that has a stationary phase comprising a strong cation exchange resin in the calcium form (Bio-Rad Aminex HPX-87C, 300×7.8 mm at 85° C.) and an eluent comprising 3 mM $Ca(H2PO4)2 \cdot H2O$ and 0.015 M H3PO4 (pH=2.2). An UV3000 system was used as detector. The water content was determined using the Karl Fisher titration procedure (KF titration) which is extensively described in handbooks and literature. As base imidazole (Hydranal composite) was used. Magnesium was determined by atomic absorption spectroscopy (AAS) on a flame AAS Varian SpectrAA 300 (including PC with SpectrAA software). The solid crystals were dissolved in nitic acid solution. Chloride content was determined by titration with silver nitrate whereby the silver chloride precipitates quantitatively. The end point is determined potentiometrically using a silver ring electrode. The results confirmed that the composition of the crystals matched with that of $MgCl_2 \cdot MgL_2 \cdot 4H_2O$.

Example 2

A lactic acid-containing magnesium chloride solution with a magnesium chloride concentration of 18.2 wt. % and a lactic acid concentration of 2.3 wt. % was prepared by mixing appropriate amounts of magnesium chloride hexahydrate ($MgCl_2 \cdot 6H_2O$), double crystallized (S)-Lactic acid crystals and demineralized water. Said solution was subjected to a first evaporation step where water was evaporated at a temperature of 65-80° C. and a pressure of 0.35 bar, to form a lactic acid-containing magnesium chloride solution with a magnesium chloride concentration of 28 wt. % and a lactic acid concentration of 3.5 wt. %. This solution was subjected to a further evaporation step, at a temperature of 80° C. and a pressure of 0.35 bar, resulting in the formation of a slurry of 9 wt. % of solid $MgCl2 \cdot MgL2 \cdot 4H2O$ in a magnesium chloride solution with a magnesium chloride concentration of 32 wt. % magnesium chloride.

The slurry was subjected in a centrifugation step and the obtained cake was washed with methanol (3×cake volume) and subsequently dried at 70° C. for 1 h. This isolated cake comprised many needle-shaped crystals, with a solids content of above 90 wt. %, and a lactic acid concentration of below 0.4 wt. %. The ratio of the weight of dried cake and weight of suspension was about 9%. The dried cake was analysed using the methods described in example 1 for magnesium (w %, AAS), lactic acid (w % as lactic acid, HPLC), and chloride (w %, titration) inclusion amount and said amounts were found to match with the theoretical values of $MgCl2 \cdot MgL2 \cdot 4H2O$. This also proved that the double salt concentration obtained after evaporative crystallization step was about 9%.

The invention claimed is:

1. A Process for removing lactic acid from an aqueous lactic acid-containing magnesium chloride solution, the weight ratio of magnesium chloride to lactic acid in the aqueous lactic acid-containing magnesium chloride solution being at least 1:1, the process comprising the steps of
subjecting the aqueous lactic acid-containing magnesium chloride solution to an evaporation step, resulting in the formation of a slurry of $MgCl_2 \cdot MgL_2 \cdot 4H_2O$ in an aqueous magnesium chloride solution,
subjecting the slurry to a solid-liquid separation step, to separate the solid $MgCl_2 \cdot MgL_2 \cdot 4H_2O$ from the aqueous magnesium chloride solution, resulting in the removal of lactic acid from the aqueous lactic acid-containing magnesium chloride solution in the form of $MgCl_2 \cdot MgL_2 \cdot 4H_2O$.

2. The process according to claim 1, wherein the weight ratio of magnesium chloride to lactic acid is at least 1.5:1.

3. The process according to claim 1, wherein the lactic-acid containing magnesium chloride solution has a magnesium chloride concentration in the range of 5 to 35 wt. %.

4. The process according to claim 1, wherein the evaporation step is carried out in one or more steps, at a temperature in the range of 50-200° C., or at reduced pressure.

5. The process according to claim 1, wherein evaporation is continued until the solution has a magnesium chloride concentration in the range of 30-47 wt. %.

6. The process according to claim 1, wherein the slurry of $MgCl_2 \cdot MgL_2 \cdot 4H_2O$ in a magnesium chloride solution comprises at least 2 wt. % of $MgCl_2 \cdot MgL_2 \cdot 4H_2O$ and at most 50 wt. % of $MgCl_2 \cdot MgL_2 \cdot 4H_2O$.

7. The process according to claim 1, wherein the magnesium chloride solution obtained from the separation step has a magnesium chloride concentration in the range of 35-47 wt. %, and/or at most 47 wt. %.

8. The process according to claim 1, wherein the lactic acid concentration in the magnesium chloride solution obtained from the separation step is at most 1 wt. %.

9. The process according to claim 1, wherein a lactic acid-containing magnesium chloride solution with a lactic acid concentration of 0.5-7 wt. % and a magnesium chloride concentration of 15-25 wt. % is subjected to one or more evaporation steps, resulting in a slurry of 4-40 wt. % $MgCl_2 \cdot MgL_2 \cdot 4H_2O$ in a magnesium chloride solution with a magnesium chloride concentration of 35-47 wt. %, and the slurry is subjected to a solid-liquid separation step resulting in solid $MgCl_2 \cdot MgL_2 \cdot 4H_2O$ and a magnesium chloride solution with a lactic acid concentration of less than 0.5 wt. %.

* * * * *